United States Patent [19]

Sloma et al.

[11] Patent Number: 5,017,477
[45] Date of Patent: May 21, 1991

[54] ENHANCING DNA SEQUENCIES DERIVED FROM THE SACQ GENE

[75] Inventors: Alan Sloma, Watertown; Rosalind C. Lee, Waltham; Janice Pero, Lexington, all of Mass.

[73] Assignee: BioTechnica International, Inc., Cambridge, Mass.

[21] Appl. No.: 921,343

[22] Filed: Oct. 20, 1986

Related U.S. Application Data

[63] Continuation-in-part of Ser. No. 791,350, Oct. 25, 1985, abandoned.

[51] Int. Cl.$^5$ .................. C12N 15/03; C12N 15/63; C12N 15/75; C12N 15/67
[52] U.S. Cl. .................. 435/69.1; 435/320.1; 435/172.3; 435/252.31; 935/38; 935/74
[58] Field of Search .................. 435/68, 70, 91, 253, 435/312, 223, 317.1, 320; 536/22; 935/7, 29, 72

[56] References Cited

U.S. PATENT DOCUMENTS 4,824,222  4/1989  Furutani et al. .................. 435/172.3

FOREIGN PATENT DOCUMENTS

| | | |
|---|---|---|
| 0034470 | 8/1981 | European Pat. Off. . |
| 0074553 | 5/1983 | European Pat. Off. . |
| 0108301 | 5/1984 | European Pat. Off. . |
| 0133756 | 3/1985 | European Pat. Off. . |
| 0146743 | 7/1985 | European Pat. Off. . |
| 149241 | 7/1985 | European Pat. Off. . |
| 0154566 | 9/1985 | European Pat. Off. . |
| 0174785 | 3/1986 | European Pat. Off. . |
| 2142336 | 1/1985 | United Kingdom . |
| 8300702 | 3/1983 | World Int. Prop. O. . |

OTHER PUBLICATIONS

Tomioka et al. (1985) Biotechnology 3: 85–96.
Tomioka et al., (1984), Program of the Ninth Internat'l Spores Conference No. 111.
Uehara et al., (1974), J. Bacteriology, 119(1), 82.
Kunst et al., (1974), Biochimie 56:1481.
Nagami and Tanaka (1986), J. Bact. 166:20.
Moran et al., (1981), Cell 25:783.
Stahl and Ferrari (1984), J. Bact. 158:411.

*Primary Examiner*—Richard A. Schwartz
*Assistant Examiner*—S. Nolan
*Attorney, Agent, or Firm*—Fish & Richardson

[57] ABSTRACT

A bacterial cell transformed with a gene encoding a desired product and with an enhancing DNA sequence capable of enhancing the production of the desired product in the bacterial cell, the enhancing DNA sequence being further characterized in that it is capable of enhancing the production of an endogenous protease in a Gram-positive bacterial cell.

24 Claims, 6 Drawing Sheets

FIG. 1

```
  1 GATCTTTCAA AAAAAGGAGT GTGGAAACGG TGGAAAAGAA ATTAGAAGAA GTAAAGCAAT
 61 TATTATTCCG ACTTGAAAAT GATATCAGAG AAACAACCGA CTCATTACGA AACATTAACA
121 AAAGCATTGA TCAGCTCGAT AAATTCTCAT ATGCAATGAA AATTTCTTAA TATACGTTGG
181 AAACAAGTCT TTTTTTTGTG CATTTTTCAC CCATTTCATG GATAAAGTAT TATACGATTG
241 TTAAAAAACG AAAAACCTGC TGTCTTTCAT CACCTGCATT TAGTAAAATA GAATGGGAGG
301 GTGAAGACAA TTATTGAGCA AATGTGTTTA GATGCCGAAA CGATTAAAGG GAAGATGAAG
361 GAAATTGTTG GGGATAAAGT CGATAATCTA CATTTAGAAG AGACTCTTTT GACCTTCATT
421 AATGAAAAGA AGCACTTTTC ATTCGGTGTC CTTGCTTTCC AGCATTATGT TGCTTTTAAG
481 GGTACACATT CCTCGGAAAT CACACTACTG GCCGCTGGAA TTGAACTTTT AATTTTAGCT
541 TTTGATATTT TTGACGATAT TGAAGATGAA GATAACTTTA ATAAGGCATG GATGCAAACT
601 GACCATGCTA TATCCCTGAA TGCGGCTACT TCTCTGTATT CAATAAGCCT GCAAGCCATT
661 TGTGAGCTTG AATCAAACAT CGATTTTTCA AGACTTGCAA TAAAATATGC CCTAAATGCA
721 ATGCAAGGTC AGCATAATGA TCA
```

FIG. 2(a)

Apro INSERT

Sau3A/Bcl I            Met   sacQ GENE PRODUCT
                                             |    46 AMINO ACIDS
GATCTTTCAAAAAAAGGAGTGTGGAAACG   GTG ~~~~~~ ...

|— B. amyloliquefaciens —————————————|

FIG. 2(b)

```
  1 GATCTTTCAA AAAAAGGAGT GTGGAAACGG TGGAAAAGAA ATTAGAAGAA GTAAAGCAAT
 61 TATTATTCCG ACTTGAAAAT GATATCAGAG AAACAACCGA CTCATTACGA AACATTAACA
121 AAAGCATTGA TCAGCTTTTG TCCGCGGAAT ATAATATTTT TAAAAATCAT CCCTTCAGAG
181 GAAAGCCGTG TGACGTATTC ATTAATGAAT TGCTGAAAGG ATAAACCCGC CTTCCATGTG
241 ATTCCTGCAA GCCTTGTTGG AAAATCGCCT CCCTTTGTTT CGGTCAGGCA ATATTCGAGC
301 TGATCA
```

FIG. 3(a)

Apro*INSERT                                  67 AMINO ACIDS Sau3A/Bcl I            Met   36 AMINO   31 AMINO
                                         |     ACIDS     ACIDS
GATCTTTCAAAAAAAGGAGTGTGGAAACG   GTG ~~~~~~

|— B. amyloliquefaciens ——————————|
                                                                       B. subtilis

CONSTRUCTION OF E. coli PLASMID pAS14

CONSTRUCTION OF pAL3

FIG. 6

ENHANCING DNA SEQUENCIES DERIVED FROM THE SACQ GENE

BACKGROUND OF THE INVENTION

This application is a continuation-in-part of U.S. Ser. No. 791,350, filed Oct. 25, 1985 now abandoned.

This invention relates to enhancing the expression of genes in microorganisms.

SUMMARY OF THE INVENTION

In general, the invention provides a bacterial cell transformed with a gene encoding a desired product and with an enhancing DNA sequence capable of enhancing the production of the desired product in the bacterial cell, the enhancing DNA sequence being further characterized in that it is capable of enhancing the production of an endogenous protease in a Gram-positive bacterial cell.

In preferred embodiments, the enhancing DNA sequence includes DNA derived from or substantially identical to a DNA sequence of a different bacterial cell; one or both bacterial cells are Gram-positive; the bacterial cells, independently, are chosen from *Bacillus subtilis*, *B. licheniformis*, *B. amyloliquefaciens*, *B. polymyxa*, *B. stearothermophilus*, *B. thermoproteolyticus*, *B. coagulans*, *B. thuringiensis*, *B. megaterium*, *B. cereus*, *B. natto*, *B. acidocaldarius*, *Clostridium perfringens*, or *C. tetanus*; the desired product is a protein, e.g., a naturally-secreted prokaryotic protein such as a protease, an alkaline phosphatase, an amylase or another enzyme, or a prokaryotic protein or peptide such as an enzyme or a hormone; and the enhancing DNA sequence is carried on a multicopy plasmid and/or is integrated into the chromosome of the bacterial cell, which is most preferably of a *B. subtilis* strain.

The enhancing DNA sequences of the invention are of two general classes: (1) those which contain two adjacent DNA sequences, each of which is derived from or substantially identical to naturally occurring DNA sequences of a different strain of Gram-positive bacteria; and (2) those which contain only DNA derived from or substantially identical to a naturally occurring DNA sequence of one Gram-positive bacterial strain. ("Substantially identical to" means similar enough in sequence to function as the naturally occurring sequence functions.)

Enhancing DNA sequences of the two classes listed above are isolated by different methods. Generally, the enhancing sequences of the first class are isolated by the steps of: (a) providing a cloning vector containing a fragment of the *B. amyloliquefaciens* DNA sequence GATCTTTCAAAAAAAGGAGTGTGGAAACGGTGGAAAAGAAATTAGAAGAAGTAAAGCAATTATTATTCCGACTTGAAAAT GATATCAGAGAAACAACCGACTCATTACGAAACATTAACAAAAGCATTGATCA (which comprises a portion of the sacQ gene, described in Yang et al. (1986) J. Bacteriol. 166, 113–119 and which encodes a portion of the sacQ gene product); (b) digesting the DNA of a Gram-positive bacterial strain other than *B. amyloliquefaciens* to give a plurality of DNA fragments; (c) inserting the fragments into the cloning vectors; (d) transforming bacteria of a bacterial strain with the cloning vectors; (e) assaying protease production in the transformed bacteria; (f) selecting bacteria exhibiting increased protease production; and (g) isolating the enhancing DNA sequence from the cells exhibiting increased protease production, the enhancing DNA sequence being the *B. amyloliquefaciens* DNA together with the inserted non-*B. amyloliquefaciens* DNA.

Generally, enhancing DNA sequences of the second class, which enhance the production of a protease in a first Gram-positive bacterial strain, are isolated by the steps of (a) digesting the DNA of a different Gram-positive bacterial strain to give a plurality of DNA fragments; (b) inserting the fragments into cloning vectors; (c) transforming bacteria of the bacterial strain with the cloning vectors; (d) assaying protease production in the transformed bacteria; (e) selecting bacteria exhibiting increased protease production; and (f) isolating the enhancing DNA sequence from the bacteria exhibiting increased protease production.

Because the enhancing sequences of the invention function by encoding protein products which enhance the production of the desired product, even greater enhancement of that product can be achieved by placing the enhancing sequence under the transcriptional control of a strong promoter to effect the production in the host bacterial cell of increased quantities of the protein product of the enhancing sequence.

The invention provides enhanced expression of desired genes in bacteria such as B. subtilis in a simple, inexpensive manner which does not require modifications in the fermentation conditions of the bacteria, and which does not affect the properties of the desired end-products.

Other features and advantages of the invention will be apparent from the following description of the preferred embodiments thereof, and from the claims.

DESCRIPTION OF THE PREFERRED EMBODIMENTS

The will first briefly be described.

Drawings

Structure of Apro and Apro*

Figure 1:
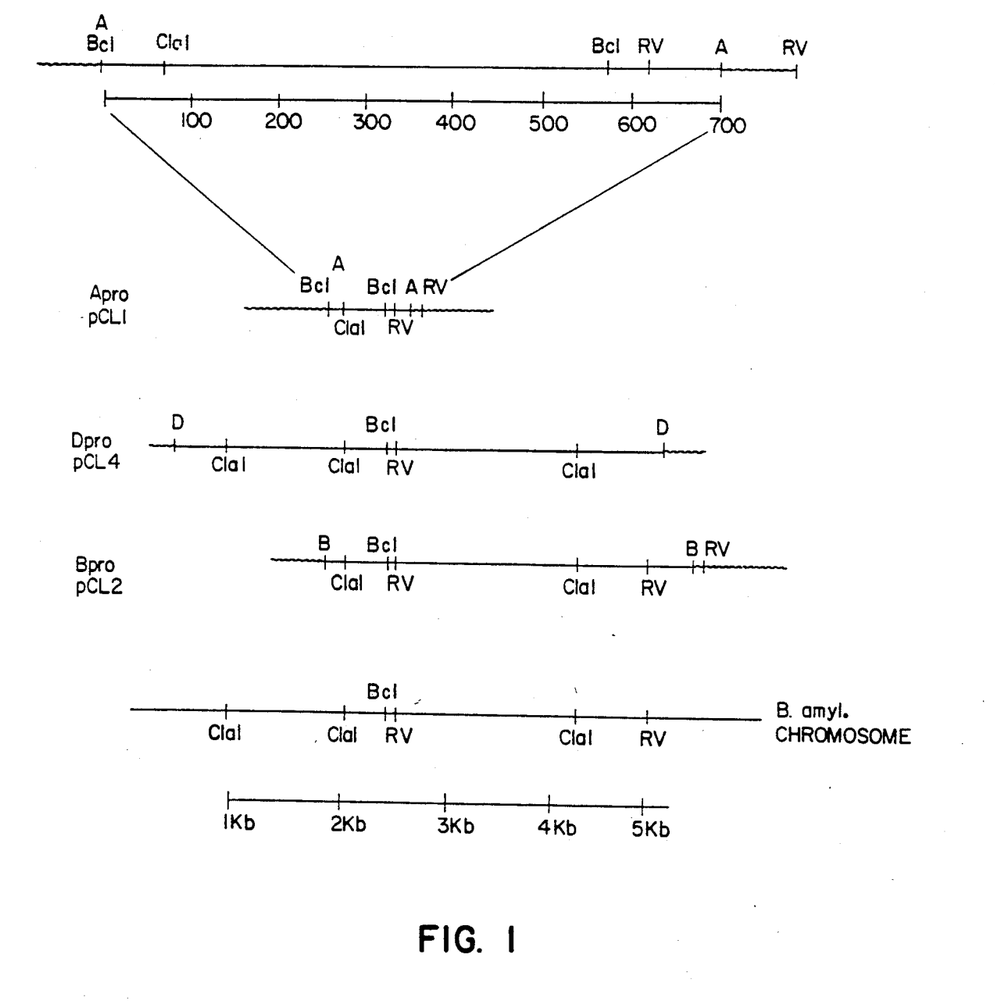
FIG. 1 is a diagrammatic representation of the region of the *Bacillus amyloliquefaciens* chromosome containing an enhancing DNA sequence, termed the Apro DNA sequence.
Figure 2A:
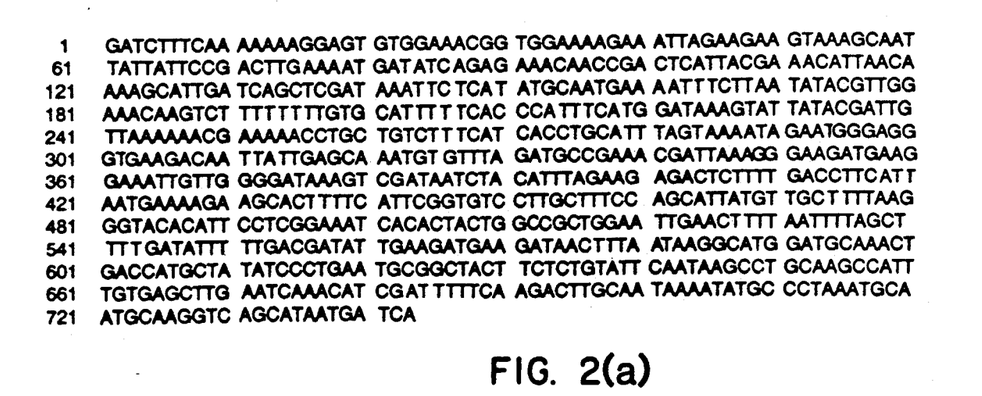
FIG. 2(a) is the nucleotide sequence of Apro.
Figure 2B:
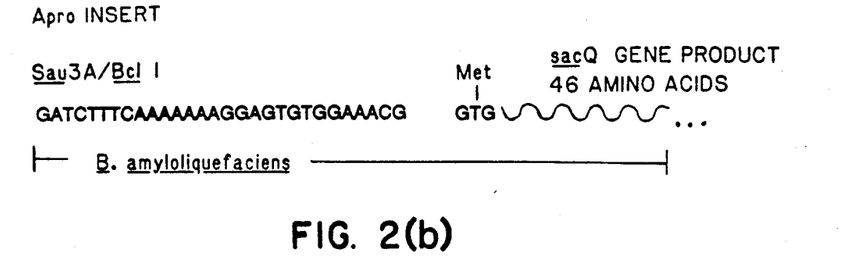
FIG. 2(b) shows its left end.
Figure 3A:
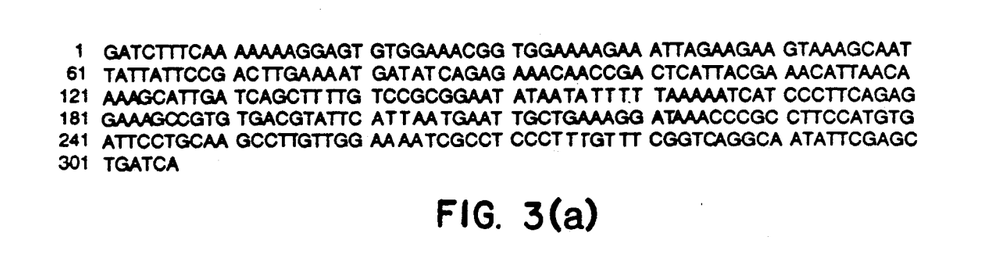
FIG. 3(a) is the nucleotide sequence of another enhancing DNA sequence, termed the Apro sequence.
Figure 3B:
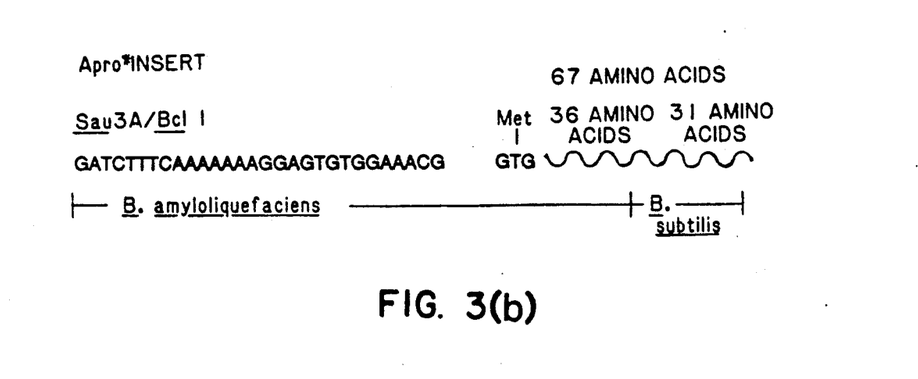
FIG. 3(b) shows its left end.

FIGS. 1-3 relate to two particular enhancing DNA sequences of the invention, designated Apro and Apro*. Apro is made up entirely of chromosomal *B. amyloliquefaciens* DNA, i.e., it is in the second class of enhancing DNA sequence, above. Apro*, containing *B.*

*amyloliquefaciens* DNA and *B. subtilis* DNA, is in the first class, above.

Referring to FIG. 1, the lower portion of the Figure represents a portion of the chromosome of *B. amyloliquefaciens*. Restriction enzyme sites are shown as Bcl for BclI, ClaI for ClaI and RV for EcoRV. FIG. 1 also shows the structure of three inserted DNA sequences, Apro, Bpro, and Dpro, which are carried on the plasmids pCL1, pCL2, and pCL4, respectively. A, B, and D represent the approximate positions of Sau3A restriction sites at the ends of the inserts Apro, Bpro and Dpro, respectively. Approximate sizes, in kilobase pairs, are shown on the lower line.

Referring to FIGS. 2(a) and 3(a), the nucleotide sequences of the Apro and Apro* enhancing DNA sequences are given. These ar numbered from the 5' end starting with the G base of the Sau3A restriction site at the end of the insert DNA. The first 133 bases of both sequences (reading from left to right) are identical and represent the Sau3A-EcoRV-BclI fragment represented in FIG. 1 as A-RV-Bcl (reading, in FIG. 1, from right to left). The positions of these restriction sites correspond to bases 0, 81, and 128, respectively. The two sequences are also homologous at three base pairs following the BclI site.

Cloning of Apro

A library of *B. amyloliquefaciens* chromosomal DNA was constructed in *B. subtilis* by partially digesting the chromosomal DNA with Sau3A and ligating it into a complete BclI digest of the positive selection plasmid pBD214. The ligated DNA was used to transform *B. subtilis* strain BD393, and 6,300 transformed colonies were obtained, selecting for resistance to trimethoprim and chloramphenicol. These colonies were patched onto TBAB plates containing 5 ug/ml chloramphenicol and 1.5% casein. After 12 hours at 37° C. three colonies showed large halos, indicating increased protease production. These colonies were found to contain plasmids, designated pCL1, pCL2, and pCL4, having inserted *B. amyloliquefaciens* chromosomal DNA which we have designated, respectively, Apro, Bpro, and Dpro.

The plasmid DNA of these colonies was isolated and restriction analysis revealed inserts of 750 base pairs, 2.5 kilobase pairs, and 4 kilobase pairs in pCL1, pCL2, and PCL4, respectively. The restriction maps of these three clones do not correspond to that reported for either the neutral or alkaline protease genes from *B. amyloliquefaciens*, and the DNA sequence of Apro (FIG. 2), determined by standard procedures, did not match the reported sequences of these protease genes.

The restriction maps of pCL1, pCL2, and pCL4 are shown in FIG. 1, the inserts being represented as areas between the letters A, B and D, respectively. From these data, and from Southern blot analyses on *B. amyloliquefaciens* chromosomal DNA, it was determined that all three plasmids contained overlapping fragments of a continuous segment of the *B. amyloliquefaciens* chromosome. In pCL1 the right hand end (with respect to FIG. 1) of the cloned fragment is defined by a BclI site, which is recreated during the cloning process.

Protease Production pCL1 was transformed into four competent *B. subtilis* strains: (1) wild type; (2) neutral-protease-deleted; (3) subtilisin-deleted; and (4) subtilisin and neutral-protease-deleted strains. Protease activity was measured using standard hide-powder azure assays. In wild type strains both alkaline and neutral protease activities were stimulated by pCL1; in the neutral-deleted strain only subtilisin activity was stimulated, in the subtilisin-deleted strain only neutral protease activity was stimulated, and in the double protease deleted strain, no stimulation was observed. The stimulation, when observed, was 5 to 10 fold over wild type levels

Cloning of Apro*

A preparation of pCL1 was digested with BclI, to give two fragments of approximately 610 base pairs and 5 kilobase pairs, respectively. The DNA was ligated to itself, and the ligated DNA used to transform *B. subtilis* strain IS75, and the resulting colonies patched onto casein plates as described above. Colonies with twice the halo size of the original Apro clone were selected. Restriction enzyme and Southern analysis demonstrated that they contained a plasmid containing a *B. subtilis* BclI fragment of 170 base pairs; this fragment, which we have shown to be derived from contaminating *B. subtilis* chromosomal DNA present in the pCL1 preparation, has no demonstrable homology with the 610 base pair BclI fragment of Apro. We have called this plasmid pAS20. As shown in FIG. 3, the Apro* sequence contains, upstream from the *B. subtilis*-derived fragment, the 133 base pair Sau3A-EcoRV-BclI *B. amyloliquefaciens* fragment which is also present in Apro; this fragment of Apro was not removed when pCL1 was digested with BclI.

Protease assays on the above-described protease deleted and wild type strains of *B. subtilis* demonstrated that pAS20 stimulated protease production 25 to 50 fold over wild type levels.

Cloning of Additional Regulatory Sequences

Additional regulatory DNA sequences with similar properties can be isolated from other Gram-positive species, particularly Bacillus species, using the same techniques employed in obtaining Apro and Apro*. The following example, using *B. polymyxa*, is illustrative of the method, described above, of isolating an enhancing DNA sequence made up entirely of DNA of one species.

A BglII digest of *B. polymyxa* was ligated to pBD214 that had been digested with BclI. The resulting DNA was transformed into *B. subtilis* strain BD393, and clones showing increased protease production on casein plates were selected in the same manner as described above for Apro. From the 1500 colonies picked, two hyperproducers were found. They appear to have identical restriction maps, and have an insert size of about 6kb.

The other general enhancing sequence production method, employing a portion of the Apro sequence to generate enhancing DNA sequences containing DNA derived from two species (*B. amyloliquefaciens* and one other species) is illustrated by the following example, employing *B. polymyxa*.

pCL1 was digested with BclI and re-ligated. This removed the 610 base pair BclI fragment while retaining the 133 bp Sau3A - EcoRV - BclI fragment from *B. amyloliquefaciens* common to both Apro and Apro*. We have called this 133 bp sequence Apro$^\Delta$; the plasmid carrying it, called pAS21, was restricted with BclI and then ligated to chromosomal DNA from *B. polymyxa* which had been completely digested with BclI. The resulting DNA was transformed into wild type *B. sub-* tilis strain IS75 and screened for protease enhancement. This produced two additional clones which, like pAS20, contained enhancing DNA sequences which were hybrids of DNA from *B. amyloliquefaciens* and another species.

All of these enhancing DNA sequences of both classes act in a similar fashion in that they specifically increase protease production when transformed into strains of *B. subtilis* containing the subtilisin or neutral protease genes. However, apart from the 133 base pair *B. amyloliquefaciens* sequence present on some of the enhancing sequences, the enhancing sequences, as tested by Southern blot analysis, do not exhibit homology. Neither Apro nor Apro* sequences hybridize to the enhancing sequences derived wholly from *B. polymyxa*, or to any region on the *B. polymyxa* chromosome.

Plasmid pAS21 has no enhancing activity of its own, although the Apro[66] *B. amyloliquefaciens* insert is, as is mentioned above, a preferred component of enhancing sequences. pAS21 (or any other cloning vector carrying the Apro[66] sequence) can therefore be used in the manner described above to isolate enhancing sequences from other Gram-positive bacterial species. DNA from a desired cell can be digested with BclI, or with another enzyme such as Sau3A, BamHI, or BglII, and the resultplace a gene encoding a desired protein downstream from a *B. subtilis* protease promoter such that it is under the transcriptional control of this promoter. One preferred construction is one in which the desired protein-encoding gene is located within, or downstream from, and in reading frame with, the DNA region encoding the protease signal sequence, which in turn is located downstream from the protease promoter. This construction not only places transcription of the desired gene under the control of the protease promoter, but also effects the secretion of the desired protein, by virtue of the fused protease signal sequence. An enhancing sequence (preferably carried on a multicopy plasmid) can be introduced into the same cells, to increase the level of expression from the protease regulatory DNA, and thus increase the production and secretion of the desired foreign gene product.

The promoter for the subtilisin gene of *B. subtilis* is an appropriate promoter for such a construction since the subtilisin gene contains an HpaI site in the middle of its signal sequence at which a synthetic linker (e.g.,

```
5'                                                                                    3'
A ACG TTA ATC TTT ACG ATG GCG TTC AGC AAC ATG TCT GCG CAG GCT GCA
T TGC AAT TAG AAA TGC TAC CGC AAG TCG TTG TAC AGA CGC GTC CG      )
3'                                                                                    5'
``` can be inserted. This linker recreates the subtilisin signal sequence and provides a PstI site to which DNA can be ligated. The putative promoter and signal sequence of the *B. subtilis* subtilisin gene up to the HpaI site is

GATATACCTAAATAGAGATAAAATGTGAAAAAAATGGGTCTAG

TAAAATATTATTCCATCTATTACAATAAATTCACAGAATAGTCTTTTAAGTAAG

```
                                                  fMet Arg Ser Lys Lys Leu Trp
TCTACTCTGAATTTTTTTAAAAGGAGAGGGTAAAGA GTG AGA AGC AAA AAA TTG TGG
```

```
Ile Ser Leu Leu Phe Ala Leu
ATC AGC TTG TTG TTT GCG TTA,
``` ing DNA ligated into the BclI site of pAS21 as described above. The resulting DNA is transformed into wild type *B. subtilis* and clones exhibiting protease enhancement identified as described above. Any clones so identified will carry DNA that is a hybrid of all or a portion of the original 133 base pair *B. amyloliquefaciens* DNA (Apro[Δ]) and DNA from the other species.

Sequencing

The sequences of Apro and Apro* are given in FIGS. 2(*a*) and 3(*a*), respectively. The first 133 base pairs of each are identical and correspond to the Sau3A-EcoRV-BclI fragment of *B. amyloliquefaciens* DNA (Apro[Δ]). The sequences are also homologous at the three base pairs following the Bcl site. The remainder of the DNA sequences show no more than a 12 base pair section of homology to each other. Apro encodes the 46 amino acid product of the sacQ gene of *B. amyloliquefaciens* which is nearly identical to the *B. subtilis* sacQ gene as described in Yang et al., id. Apro* encodes a 64 amino acid fusion protein containing the first 36 amino acids of the *B. amyloliquefaciens* sacQ gene product fused to 28 amino acids encoded by *B. subtilis* DNA.

Construction of an Expression-Secretion Vector

The DNA sequences of the invention stimulate the production of proteases in *B. subtilis*. It is possible to with the arrow indicating the HpaI site.

In one such construction, described in detail below, a *Bacillus licheniformis* structural gene for alpha-amylase, fused to a gene for a desired product known as APIII (discussed below) was inserted at the PstI site so that the promoter and signal sequence of subtilisin and the structural genes of the alpha-amylase and APIII are in frame. The introduction of an enhancing DNA sequence into a cell containing this fusion was found to enhance the expression of the subtilisin/alpha-amylase/APIII gene fusion. Any other desired gene can be fused in frame to the carboxy-terminal end of the alpha-amylase gene to create a gene fusion encoding a stable hybrid protein, the expression of which is enhanced by the enhancing DNA sequence. The alpha-amylase portion of the hybrid protein will, it is believed, protect the desired protein or peptide portion of the hybrid from degradation; after purification, the alpha-amylase portion can be removed, using standard techniques. Other genes could be used in place of or fused to the gene for alpha amylase, e.g., genes for medically useful peptides or proteins, e.g., genes for hormones or antiviral proteins, e.g., genes for other naturally-secreted prokasyotic enzymes.

Figure 4A:
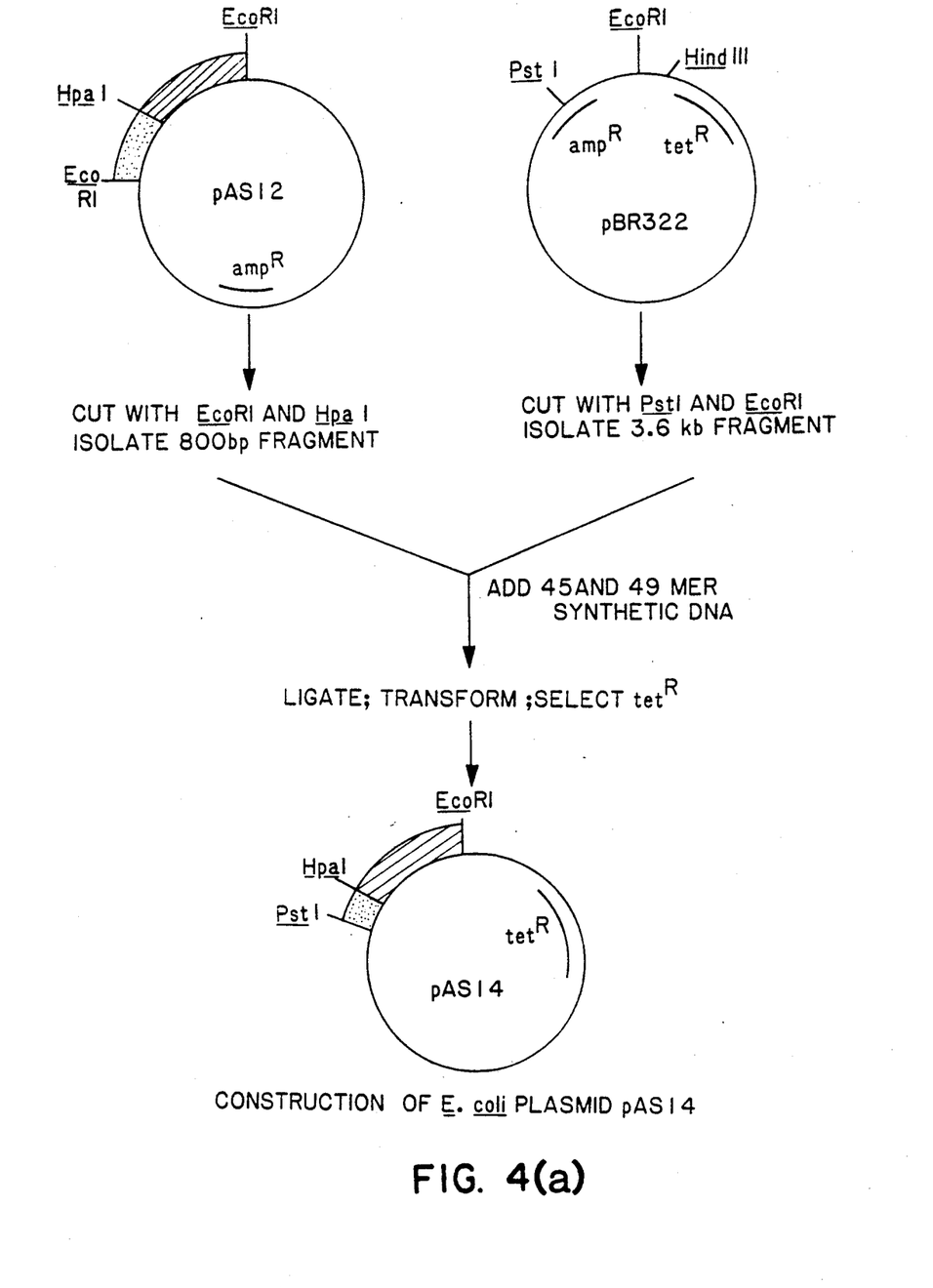
FIGS. 4(a) and 4(b) are illustrations of the construction of pAS15, a plasmid in which a fusion of two structural genes (alpha-amylase and APIII, described below) is under the transcriptional control of the *B. subtilis* subtilisin promoter.
Figure 4B:
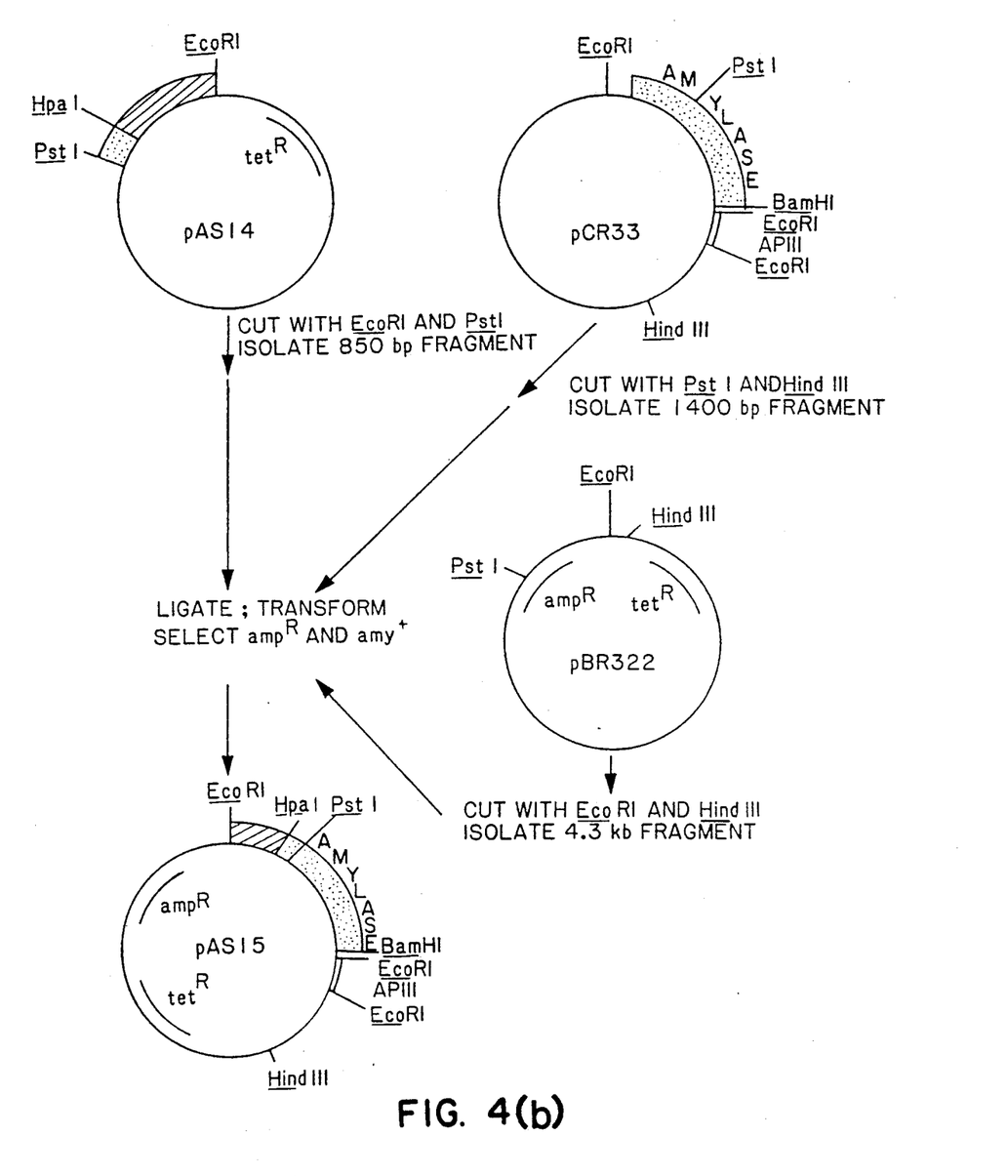

Referring to FIGS. 4 (*a*) and 4(*b*), plasmid pAS15, containing the above-mentioned amylase/APIII construction inserted into the PstI site of the subtilisin gene, was constructed as follows.

The source of the amylase/APIII fusion was plasmid pCR33, described in Stephens et al. U.S. Ser. No. 845,864, assigned to the same assignee as the present application, hereby incorporated by reference. APIII is, as is described in Stephens et al., id, a derivative of human natriuretic factor, and is a peptide which can be administered to human patients to control hypertension and regulate serum sodium and potassium levels.

Referring to FIG. 4 (a), a portion of the B. subtilis subtilisin gene was cloned on pAS12. An 800 bp EcoRI-HpaI fragment (Fragment E in Stahl & Ferrari, 1984, J. Bact. 158: 411-418) containing the subtilisin promoter and signal sequences was isolated from pAS12. The sequence of the putative promoter and the beginning of the signal sequence (up to the HpaI site) is shown in Stahl & Ferrari (bases 1-177 in FIG. 2 of that paper) and is also shown above. Synthetic linkers (49+45 mers, sequence given above), which finished the signal sequence of subtilisin and created a PstI site at the 3' end, were ligated to the above fragment and the 3.6 kb EcoRI-PstI backbone from pBR322 containing the Tet$^R$ gene. The ligated DNA was then introduced into E. coli cells, strain JM107, and Tet$^R$ transformants were selected which were shown to have the correct structure of the finished signal sequence. Plasmid pAS14 was isolated from one of these transformants.

Referring to FIG. 4 (b), the 850 bp EcoRI-PstI fragment from pAS14 containing the subtilisin promoter and completed signal sequence was isolated and ligated to a 1.4 kb PstI-HindIII fragment from pCR33, coding for the amylase-APIII fusion protein, and the 4.3 kb EcoRI-HindIII pBR322 backbone containing the Tet$^R$ and Amp$^R$ genes. Amp$^R$ transformants were obtained by transformation of JM107 cells with the ligated DNA and those found to produce large halos when plated on starch-azure indicator plates were selected These contained the subtilisin promoter-subtilisin signal sequence-amylase-APIII fusion in the correct orientation. Plasmid pAS15 was isolated from one of these transformants.

A chloramphenicol resistance (CAT) gene selectable in B., subtilis was placed on pAS15 to allow chromosomal integration, as follows. pAS15 was partially digested with SalI and DNA that had been singly cut was isolated. This DNA was ligated to a 1.3 kb SalI fragment from PEccI (an E. coli plasmid containing the CAT gene) and the ligated DNA was transformed into JM107. Amp$^R$ transformants were screened for Tet$^S$ and Cm$^R$ colonies; plasmid DNA was isolated from a colony (pAS16) that had the correct phenotype. This DNA was then used to integrate the fusion construction into the B. subtilis chromosome. Transformation of B. subtilis resulted in colonies which, when grown on starch-azure plates, produced small halos, indicating secretion of the fusion protein.

Competent cells containing PAS16 were made and transformed with pApro*-Tet (Apro* with a Tet$^R$ gene) and a control plasmid (p214-Tct). When plated on starch-azure plates, cells containing pApro*-Tet produced a large halo indicating secretion of the amylase-APIII fusion protein.

The integration of the CAT gene into the chromosome next to the subtilisin-amylase-APIII DNA construction described above permitted selecting for colonies that grow at higher concentrations (60-90 ug/ml) of chloramphenicol and therefore have an increased copy number of the gene fusion, and thus are capable of increased expression and secretion of the fusion product.

Enhancing the Expression of Apro*

Figure 5:
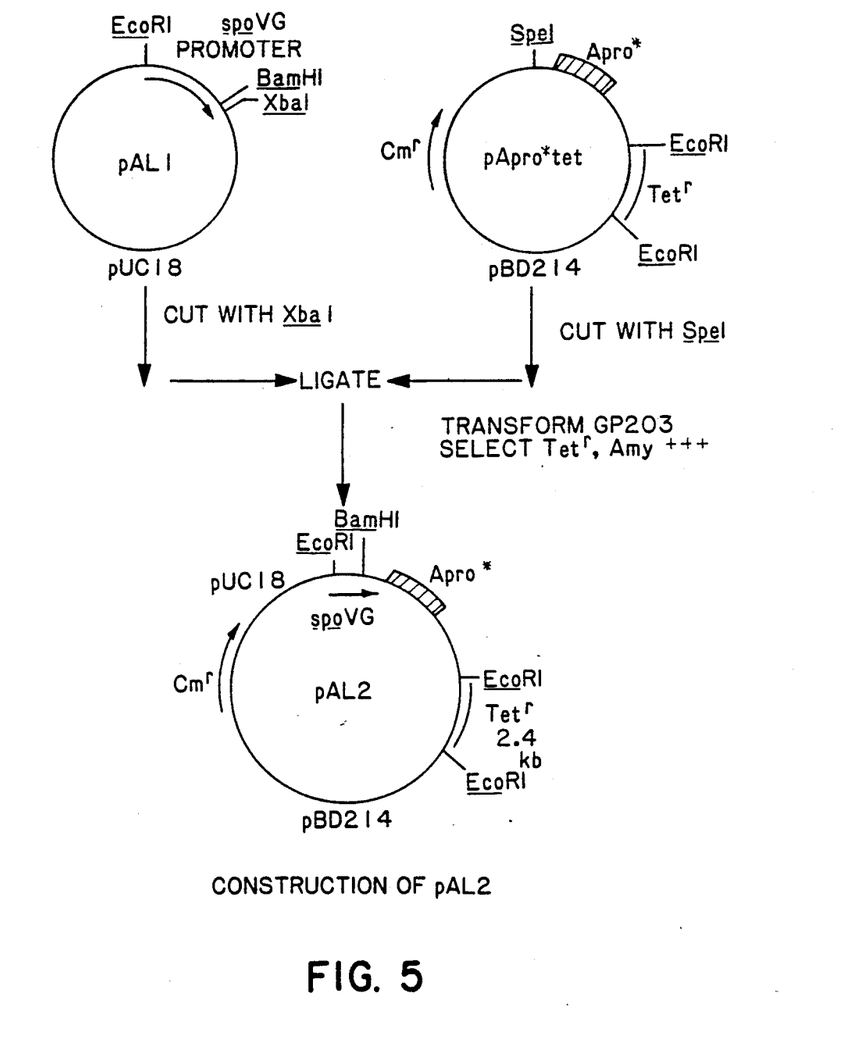
FIG. 5 is an illustration of the construction of pAL2, a plasmid containing Apro* under the transcriptional control of a strong sporulation promoter, the spoVG promoter.

Referring to FIG. 5, a strong sporulation promoter was placed in front of Apro* as follows. The spoVG promoter (also known as the 0.4 kb gene promoter), a strong sporulation promoter described in Moran et al. (1981) Cell 25, 783-791, was isolated as a 1.7 kb EcoRI-XbaI fragment from E. coli plasmid pAL1. The sequence of this promoter is given in Moran et al., id. This fragment was ligated with SpeI-cut pApro*-tet. SpeI cuts pApro*-tet approximately 100 bp before the start of the Apro* gene. The ligated DNA was then used to transform the B. subtilis strain having the amylase-APIII fusion chromosomally integrated, as described above (strain GP203). Plasmid DNA from Tet$_r$ colonies was isolated, and one plasmid, pAL2, was found to have the spoVG promoter in the right orientation 5' to the Apro* gene. This colony also produced the largest halo on starch-azure indicator plates.

Figure 6:
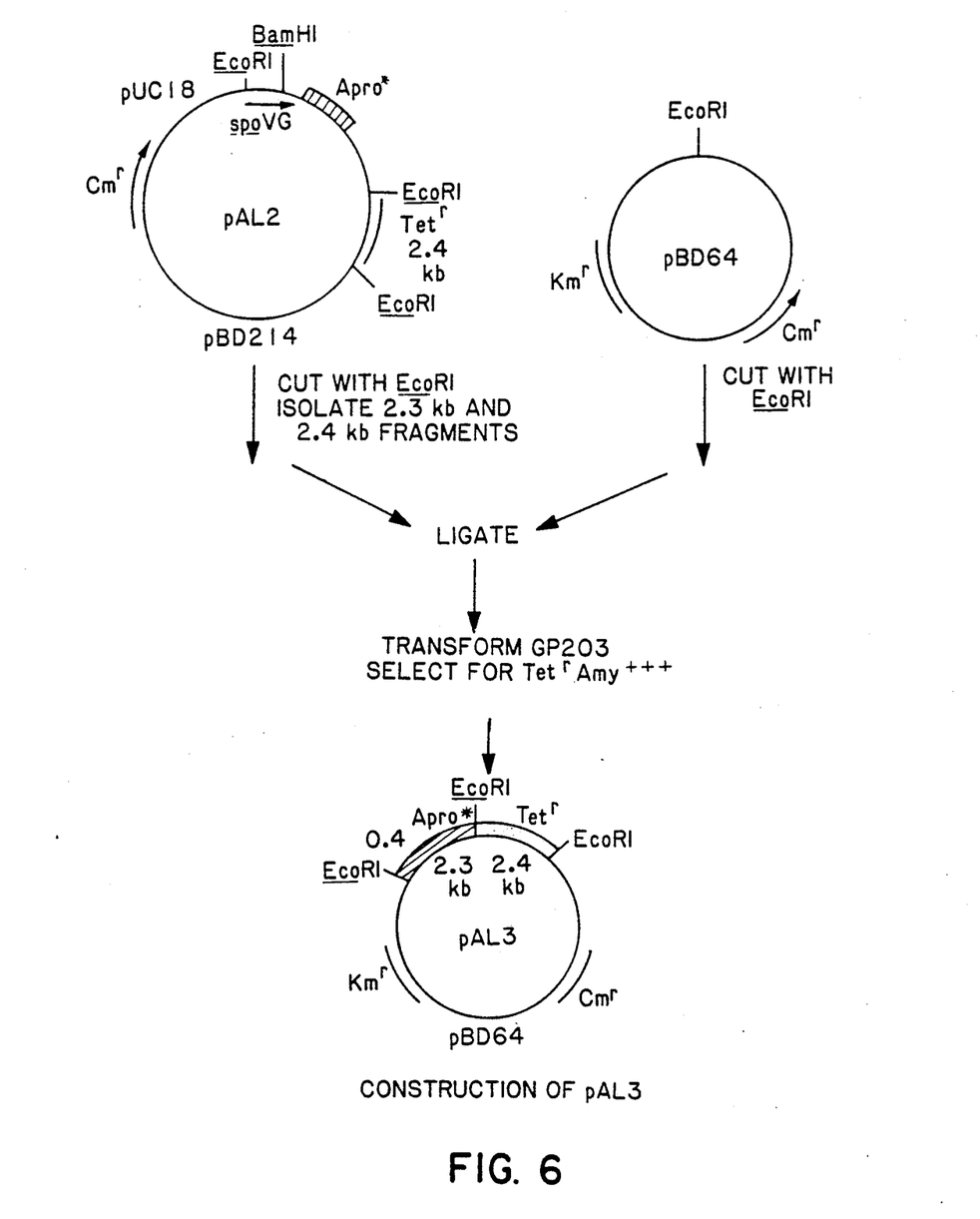
FIG. 6 is an illustration of pAL3, a derivative of pAL2 from which *E. coli* sequences have been excised.

Because pAL2 is a large plasmid (11.2 kb) containing a large section of E. coli DNA, a derivative of pAL2 that was smaller and had no E. coli sequences was constructed, as shown in FIG. 6. pAL2 was digested with EcoRI and a 2.3 kb fragment containing the spoVG promoter and the Apro gene, and a 2.4 kb fragment containing the Tet$^R$ gene, were electroeluted from a 0.8% agarose gel. The fragments were then ligated into pBD64 (publicly available; ATCC No. 37104) that had been digested with EcoRI. The ligated DNA was transformed into B. subtilis strain GP203, and plasmid DNA isolated from resulting Tet colonies. The colonies which had both EcoRI fragments inserted into pBD64, and which therefore had the spo VG-Apro* fusion, had the largest halos on starch-azure plates. Plasmid pAL3 was isolated from one such colony. When cells containing pAL3 were placed on starch-azure plates, halos indicated that this plasmid is stably maintained. pAL3 was found to significantly increase the production of protein from the constructions described herein.

OTHER EMBODIMENTS

Other embodiments are within the following claims.

For example, some enhancing sequences which one component a portion of the above-described AproΔ sequence may contain less than the entire 133 base pairs of AproΔ. The enhancing DNA sequence can be carried on any suitable phage or plasmid vector, which can remain episomal or can integrate into the host cell chromosome. Any suitable Gram-positive host cells can be used, e.g., Bacillus species which are already high producers of commercial proteases; in these host strains, there is no need to transform the host cells with a foreign gene, since the desired gene for the protease is endogenous to the host. Transformation of host cells can be carried out using either protoplasts or competent cells. The sacQ gene from any Bacillus species can be used as the source of all or a portion of the enhancing sequence, e.g., the sacQ gene of B. subtilis and B. licheniformis.

What is claimed:

1. A vector comprising a hybrid DNA sequence capable of enhancing the expression of a protease gene in a Bacillus cell, said hybrid DNA sequence including
    a first sequence comprising the sacQ DNA sequence

GATCTTTCAAAAAAAGGAGTGTGGAAACGGTGGAAA

AGAAATTAGAAGAAGTAAAGCAATTATTATTCCGAC

TTGAAAATGATATCAGAGAAACAACCGACTCATTAC

GAAACATTAACAAAAGCATTGATCA, said first sequence by itself not being capable of said enhancing, said first sequence being linked in said vector 5' to 3' with a second Bacillus DNA sequence which is not a portion of a sacQ sequence.

2. A method of providing a DNA sequence capable of enhancing the production of a protease in a Bacillus strain other than a *B. amyloliquefaciens* strain, said method comprising
 (a) providing a cloning vector containing a fragment of the *B. amyloliquefaciens* DNA sequence

GATCTTTCAAAAAAAGGAGTGTGGAAACGGTGGAAA

AGAAATTAGAAGAAGTAAAGCAATTATTATTCCGAC

TTGAAAATGATATCAGAGAAACAACCGACTCATTAC

GAAACATTAACAAAAGCATTGATCA, (b) digesting the DNA of a Bacillus other than *B. amyloliquefaciens* to give a plurality of DNA fragments,
 (c) inserting said fragments into said cloning vectors adjacent to and downstream from said *B. amyloliquefaciens* fragment,
 (d) transforming bacteria of a Bacillus strain with said cloning vectors,
 (e) assaying protease production in said transformed bacteria,
 (f) selecting bacteria exhibiting increased protease production, and
 (g) isolating said enhancing DNA sequence from said cells exhibiting increased protease production, said enhancing DNA sequence comprising said B. amyloliquefaciens DNA together with said inserted non-B. amyloliquefaciens DNA.

3. A vector containing an enhancing DNA sequence isolated according to the method of claim 2.

4. The vector of claim 1, said vector including all of said first *B. amyloliquefaciens* DNA sequence, said vector further comprising, adjacent and downstream from said first sequence, the sequence

GCTTTTG TCCGCGGAAT ATAATATTTT TAAAAATCAT

CCCTTCAGAG GAAAGCCGTG TGACGTATTC

ATTAATGAAT TGCTGAAAGG ATAAACCCGC

CTTCCATGTG ATTCCTGCAA GCCTTGTTGG

AAAATCGCCT CCCTTTGTTT CGGTCAGGCA

ATATTCGAGC TGATCA.

5. The vector of claim 1, said enhancing DNA sequence being under the transcriptional control of a strong promoter.

6. The vector of claim 5, said strong promoter being a *B. subtilis* sporulation promoter 7. The vector of claim 6, said promoter being the spoVG promoter.

8. A host Bacillus cell transformed with the hybrid DNA sequence recited in claim 1 and DNA encoding a desired product.

9. The host Bacillus cell of claim 8 wherein said second DNA sequence is derived from or substantially identical to a DNA fragment of a Bacillus cell of a strain other than *B. amyloliquefaciens*.

10. The host Bacillus cell of claim 8 wherein expression of said product-encoding DNA is under the control of regulatory DNA of a protease-encoding gene of a Bacillus cell.

11. The host Bacillus cell of claim 10 wherein said regulatory DNA includes a DNA region encoding the signal sequence of said protease and said product-encoding DNA is located within or downstream from said DNA region encoding said signal sequence of said protease.

12. The host Bacillus cell of claim 9 wherein said host Bacillus cell is of a strain of:
 (a) *Bacillus subtilis*,
 (b) *B. licheniformis*,
 (c) *B. acidocaldarius*,
 (d) *B. polymyxa*,
 (e) *B. stearothermophilus*,
 (f) *B. thermoproteolyticus*,
 (g) *B. coagulans*,
 (h) *B. thuringiensis*,
 (i) *B. megaterium*,
 (j) *B. cereus*,
 (k) *B. natto*, or
 (l) *B. amyloliquefaciens*,
and wherein said second Bacillus DNA sequence is derived from or substantially identical to a DNA fragment of a Bacillus cell of a strain of, independently:
 (a) *Bacillus subtilis*,
 (b) *B. licheniformis*,
 (c) *B. acidocaldarius*,
 (d) *B. polymyxa*,
 (e) *B. stearothermophilus*,
 (f) *B. thermoproteolyticus*,
 (g) *B. coagulans*,
 (h) *B. thuringiensis*,
 (i) *B. megaterium*,
 (j) *B. cereus*, or
 (k) *B. natto*.

13. The host Bacillus cell of claim 8 wherein said desired product is a protease or an amylase.

14. The host Bacillus cell of claim 8, wherein said enhancing DNA is carried on a multicopy plasmid.

15. The host Bacillus cell of claim 8 wherein said enhancing DNA is integrated into the chromosome of said host Bacillus cell.

16. A method for producing a desired product, said method comprising culturing the host Bacillus cell of claim 10 in a culture medium and recovering the desired product from said host Bacillus cell or culture medium.

17. The method of claim 16 wherein said Bacillus strain is a strain of *B. subtilis*.

18. The method of claim 16 wherein said product-encoding DNA and said regulatory DNA are carried on a first plasmid and said enhancing DNA is carried on a second plasmid.

19. The method of claim 16 wherein said product-encoding DNA and said regulatory DNA are integrated into the chromosome of said host Bacillus cell.

20. The method of claim 16 wherein said host Bacillus cell is a *Bacillus subtilis* cell.

21. The method of claim 16 wherein said regulatory DNA includes a promoter sequence and a sequence encoding a signal sequence of said protease, said signal sequence effecting the secretion of said desired product.

22. The Bacillus cell of claim 8 wherein said protease is *B. subtilis* subtilisin.

23. The BAcillus cell of claim 8 wherein said product-encoding DNA is fused to the carboxy terminal end of Bacillus gene for alpha-amylase.

24. A vector comprising a hybrid DNA sequence capable of enhancing the expression of a protease gene in a Bacillus cell, said hybrid DNA sequence including first and second sequences, linked 5' to 3', which together comprise less than an entire sacQ sequence, said first sequence comprising a fragment of a sacQ sequence which by itself is not capable of said enhancing and said second sequence comprising a Bacillus DNA sequence which is not a portion of a sacQ sequence, said first sequence being further characterized in that, when carried on a vector which is capable of being maintained in *B. subtilis* cells and which contains, adjacent from and downstream from said first sequence, the sequence

```
GCTTTTG TCCGCGGAAT ATAATATTTT TAAAAATCAT CCCTTCAGAG

GAAAGCCGTG TGACGTATTC ATTAATGAAT TGCTGAAAGG ATAAACCCGC CTTCCATGTG

ATTCTTGCAA GCCTTGTTGG AAAATCGCCT CCCTTTGTTT CGGTCAGGCA ATATTCGAGC

TGATCA,
``` causes increased subtilisin production in said *B. subtilis* cell.

* * * * *